US009526251B2

(12) United States Patent
Asolkar et al.

(10) Patent No.: US 9,526,251 B2
(45) Date of Patent: Dec. 27, 2016

(54) **USE OF *BURKHOLDERIA* FORMULATIONS, COMPOSITIONS AND COMPOUNDS TO MODULATE CROP YIELD AND/OR CORN ROOTWORM INFESTATION**

(71) Applicant: Marrone Bio Innovations, Inc., Davis, CA (US)

(72) Inventors: Ratnakar Asolkar, Davis, CA (US); Marja Koivunen, Davis, CA (US); Pamela Marrone, Davis, CA (US); Ana Lucia Cordova-Kreylos, Davis, CA (US); Huazhang Huang, Durham, NC (US)

(73) Assignee: Marrone Bio Innovations, Inc., Davis, CA (US)

( * ) Notice: Subject to any disclaimer, the term of this patent is extended or adjusted under 35 U.S.C. 154(b) by 36 days.

(21) Appl. No.: 14/548,824

(22) Filed: Nov. 20, 2014

(65) Prior Publication Data

US 2015/0079043 A1 Mar. 19, 2015

Related U.S. Application Data

(63) Continuation-in-part of application No. 14/336,601, filed on Jul. 21, 2014, which is a continuation of application No. 13/843,971, filed on Mar. 15, 2013, now Pat. No. 8,822,193, which is a continuation-in-part of application No. 13/034,575, filed on Feb. 24, 2011.

(60) Provisional application No. 61/406,541, filed on Oct. 25, 2010, provisional application No. 61/308,287, filed on Feb. 25, 2010.

(51) Int. Cl.
| | |
|---|---|
| *A01N 63/00* | (2006.01) |
| *A01N 63/02* | (2006.01) |
| *C07D 309/14* | (2006.01) |
| *C07D 407/06* | (2006.01) |
| *C07D 413/04* | (2006.01) |
| *C07D 413/06* | (2006.01) |
| *C07D 263/32* | (2006.01) |
| *C07D 263/34* | (2006.01) |
| *C07D 493/10* | (2006.01) |
| *C07D 498/14* | (2006.01) |
| *C07D 513/04* | (2006.01) |

(52) U.S. Cl.
CPC ............ *A01N 63/00* (2013.01); *A01N 63/02* (2013.01); *C07D 263/32* (2013.01); *C07D 263/34* (2013.01); *C07D 309/14* (2013.01); *C07D 407/06* (2013.01); *C07D 413/04* (2013.01); *C07D 413/06* (2013.01); *C07D 493/10* (2013.01); *C07D 498/14* (2013.01); *C07D 513/04* (2013.01)

(58) Field of Classification Search
None
See application file for complete search history.

(56) References Cited

U.S. PATENT DOCUMENTS

| | | | |
|---|---|---|---|
| 4,808,207 | A | 2/1989 | Gottlieb |
| 5,545,542 | A | 8/1996 | Nakajima |
| 5,902,595 | A | 5/1999 | Burklow |
| 6,077,505 | A | 6/2000 | Parke |
| 6,194,194 | B1 | 2/2001 | Molloy |
| 6,384,186 | B2 | 5/2002 | Anke |
| 6,689,357 | B2 | 2/2004 | Casida |
| 7,141,407 | B2 | 11/2006 | Zhang |
| 7,393,812 | B2 | 7/2008 | Gerwick |
| 7,396,665 | B2 | 7/2008 | Ueda |
| 7,923,005 | B2 | 4/2011 | Rao |
| 2003/0082147 | A1 | 5/2003 | Gouge |
| 2004/0071663 | A1 | 4/2004 | Campos |
| 2005/0074431 | A1* | 4/2005 | Martin ............... A01N 63/00 424/93.4 |
| 2007/0191228 | A1 | 8/2007 | Li |
| 2008/0096879 | A1 | 4/2008 | Koide |
| 2009/0175837 | A1 | 7/2009 | Yuki |
| 2010/0022584 | A1 | 1/2010 | Kenyon |
| 2011/0207604 | A1 | 8/2011 | Asolkar |
| 2014/0113816 | A1 | 4/2014 | Huang |

FOREIGN PATENT DOCUMENTS

| | | | |
|---|---|---|---|
| DE | WO 2014053396 A1 * | 4/2014 | ............ A01N 43/56 |
| JP | 2007-091701 | 4/2007 | |
| KR | 2005-003400 A | 4/2005 | |
| KR | 100537389 B1 | 12/2005 | |
| WO | WO 97/20857 | 6/1997 | |
| WO | WO 01/55143 | 8/2001 | |
| WO | WO 01/55398 | 8/2001 | |
| WO | WO 2009/049378 | 4/2009 | |
| WO | WO 2013/032693 | 3/2013 | |

OTHER PUBLICATIONS

U.S. Appl. No. 14/336,601, Asolkar, not yet published.
Abdel-Mawgoud et al., "Rhamnolipids: Diversity of Structures, Microbial Origins and Roles", Applied Microbiology and Biotechnology 86: 1323-1336. 2010.
Anderson et al., "The Structure of Thiostrepton" Nature 225: 233-235. 1970.
Andra, "Endotoxin-Like Properties of a Rhamnolipid Exotoxin from *Burkholderia*(*Pseudomonas*) *Plantarii* : Immune Cell Stimulation and Biophysical Characterization" Biol. Chem. 387: 301-310. 2006.

(Continued)

*Primary Examiner* — Renee Claytor
*Assistant Examiner* — Michelle F Paguio Frising
(74) *Attorney, Agent, or Firm* — Ying-Horng Liu; Chainey P. Singleton; Marrone Bio Innovations

(57) ABSTRACT

Provided is the use of or compositions or formulations comprising *Burkholderia* species, filtrate, supernatant, extract, pesticidally active compound or metabolite derived therefrom as an insecticide, particularly against infestation of Corn Rootworm larvae, and/or as crop yield enhancer.

9 Claims, 3 Drawing Sheets

(56) References Cited

OTHER PUBLICATIONS

Figure 1:
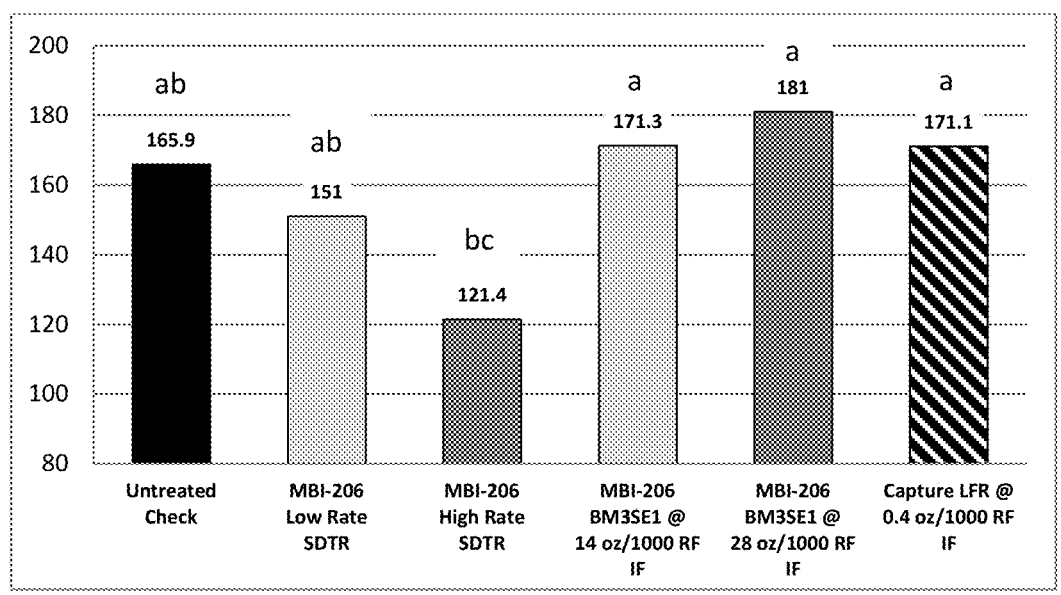
Figure 2:
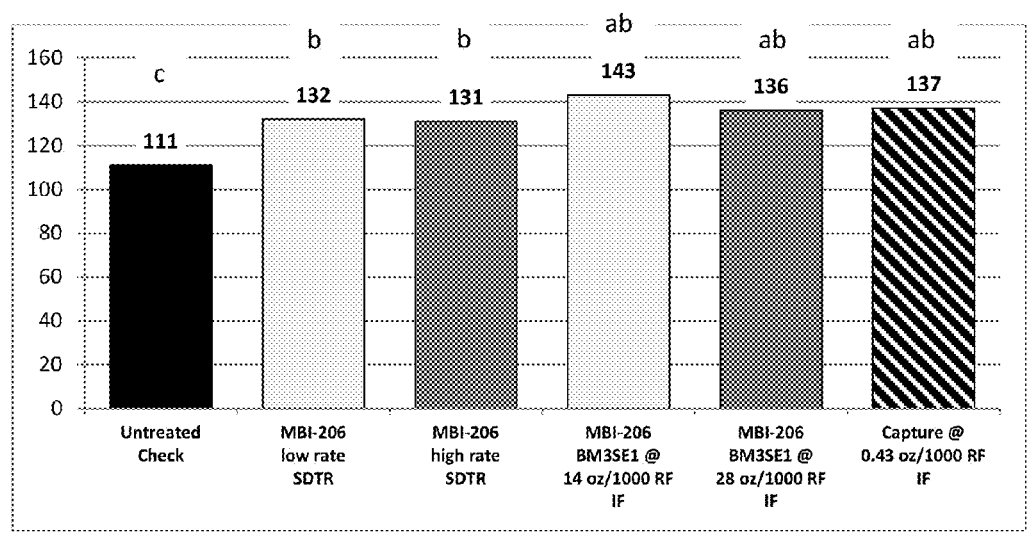
Figure 3:
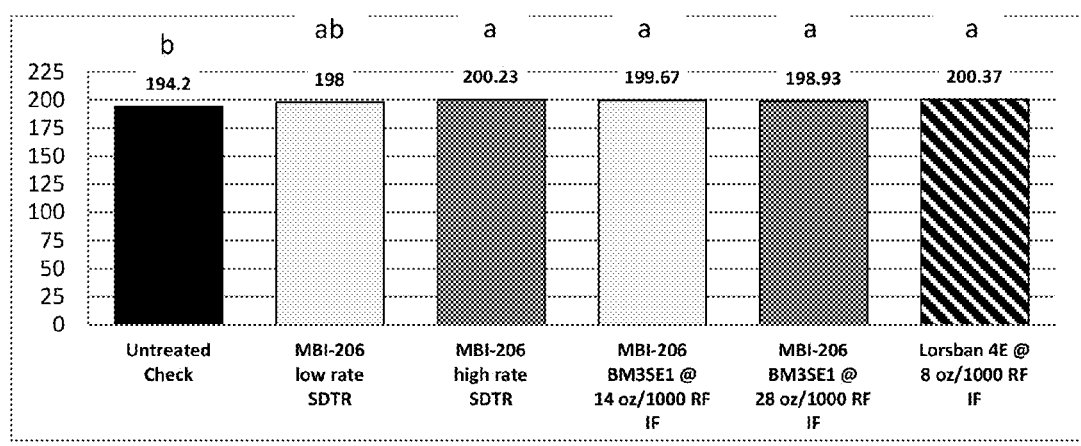

Arena et al., "The Mechanism of Action of Avermectins in Caenorhabditis Elegans—Correlation Between Activation of Glutamate-Sensitive Chloride Current, Membrane Binding and Biological Activity" J. Parasitol. 81: 286-294. 1995.
Asolkar et al., "Daryamides A-C Weakly Cytotoxic Polyketides from a Marine-Derived Actinomycete of the Genus StreptomycesStrain CNQ-085" J. Nat. Prod. 69:1756-1759. 2006.
Battu et al., "Development and Validation of RP-HPLC for the Rabeprazole Sodium in Pharmaceutical Formulations and Human Plasma", Asian J. Research Chem. 2(1): 49-51 Jan.-Mar. 2009.
Andra, "Endotoxin-Like Properties of a Rhamnolipid Exotoxin from Burkholderia (Pseudomonas) Plantarii : Immune Cell Stimulation and Biophysical Characterization" Biol. Chem. 387: 301-310. 2006.
Blodget et al., "Molecular Cloning, Sequence Analysis and Heterologous Expression of Phosphinothricin Tripeptide Biosynthetic Gene Cluster from Streptomyces Viridochromogenes DSM 40736," Antimicrobial Agents and Chemotherapy 49: 230-240. 2005.
Blodget et al., "Biosynthesis of 2-Hydroxyethylphosphonate, an Unexpected Intermediate Common to Multiple Phosphonate Biosynthetic Pathways," J. Biol. Chem. 22:23161-23168. 2008.
Burkhead et al., "Pyrrolnitrin Production by Biological Control Agent Pseudomonas Cepacia B37w in Culture and in Colonized Wounds of Potatoes", Appl. Environ. Microbiol. 60: 2031-2039. 1994.
Burkholder, "Sour Skin, a Bacterial Rot of Onion Bulbs" Phytopathology 40: 115-117. 1950.
Burkholderia andropogonis : Psuedomonas woodsii ,CW00B006C (ATCC PTA-4234) accessed from http://www.atcc.org/Products/All/PTA-4234 on Mar. 12, 2014.
Cordova-Kreylos et al., "Isolation and Characterization of *Burkholderia rinojensis*sp. nov., a Non-Burkholderia cepacia Complex Soil Bacterium with Insecticidal and Miticidal Activities," App. Env. Micro. 79(24):1-10 (2013).
Caballero-Mellado et al., "Burkholderia unamae sp. nov., an N2-fixing Rhizospheric and Endophytic Species" Int. J. Syst. Evol. Microbiol. 54: 1165-1172. 2004.
Cain et al., "Synergistic Antimicrobial Activity of Metabolites Produced by a Nonobligate Bacterial Predator," Antimicrobial Agents and Chemotherapy 47: 2113-2117. 2003.
Cashion et al., "A Rapid Method for the Base Ratio Determination of Bacterial DNA" Anal. Biochem. 81: 461-466. 1977.
Castro-Rodriguez et al., "The Glutamine Synthetase Gene Family in Populus", BMC Plant Biology 11:119. 2011.
Chen et al., "*Burkholderia nodosa* Sp. Nov., Isolated from Root Nodules of the Woody Brazilian Legumes Mimosa Bimucronata and Mimosa Scabrella" Int. J. Syst. Evol. Microbiol. 57: 1055-1059. 2007.
Cheng et al., "Melioidosis: Epidemiology, Pathophysiology, and Management" Clin. Microbiol. Rev. 18: 383-416. 2005.
Coenye et al., "Diversity and Significance of *Burkholderia*Species Occupying Diverse Ecological Niches" Environ. Microbiol. 5: 719-729. 2003.
Compant et al., "Diversity and Occurence of *Burkholderia*spp. in the Natural Environment" FEMS Microbiol. Rev. 32: 607-626. 2008.
De Ley et al., "The Quantitative Measurement of DNA Hybridization from Renaturation Rates" Eur. J. Biochem. 12: 133-142. 1970.
Deng et al., "Structural and Functional Characterization of Diffusible Signal Factor Family Quorum-Sensing Signals Produced by Members of the Burkholderia Cepacia Complex", Applied and Environmental Microbiology 76: 4675-4683. 2010.
Duke et al., "Natural Products as Sources for Herbicides: Current Status and Future Trends" Weed Res. 40: 99-111. 2000.
El-Banna et al., "Pyrrolnitrin from Burkholderia Cepacia: Antibiotic Activity Against Fungi and Novel Acivities Against Streptomycetes", J. Applied Microbiology 85: 69-78. 1998.
Eisenberg et al., "Structure—Function Relationships of Glutamine Synthetases", BBA 1477:122-135. 2000.
Gawronski et al., "Microtiter Assay for Glutamine Synthetase Biosynthetic Activity Using Inorganic Phosphate Detection", Analytical Biochemistry 327: 114-118. 2004.
Gising et al., "Trisubstituted Imidazoles as *Mycobacterium Tuberculosis*Glutamine Synthetase Inhibitors", J. Medicinal Chemistry 55: 2894-2898. 2012.
Grgurina et al., "Novel Cyclic Lipodepsipeptide from *Pseudomonas syringae*pv. lachrymans Strain 508 and Syringopeptin Antimicrobial Activities", Antimicrobial Agents and Chemotherapy, 49:5037-5045. 2005.
Guella et al., "Almazole C, a New Indole Alkaloid Bearing an Unusually 2,5-disubstituted Oxazole Moiety and its Putative Biogenetic Precursors, from a Senegalese Delesseriacean Seaweed" Helv. Chim. Acta 77: 1999-2006. 1994.
Guella et al. "Isolation, Synthesis and Photochemical Properties of Almazolone, a New Indole Alkaloid from a Red Alga of Senegal." Tetrahedron. 62: 1165-1170. 2006.
Harth et al., "An Inhibitor of Exported *Mycobacterium tuberculosis*Glutamine Synthetase Selectively Blocks the Growth of Pathogenic Mycobacteria in Axenic Culture and in Human Monocytes: Extracellular Proteins as Potential Novel Drug Targets", J. Exp. Med., 189: 1425-1435. 1999.
Harth et al., "Treatment of *Mycobacterium tuberculosis*with Antisense Oligonucleotides to Glutamine Synthetase mRNA Inhibits Glutamine Synthetase Activity, Formation of the Poly-L-Glutamate/Glutamine Cell Wall Structure, and Bacterial Replication", Proc Natl Acad Sci U S A 97:418-423. 2000.
Henderson et al., "Bongkrekic Acid. An Inhibitor of the Adenine Nucleotide Translocase of Mitochondria" J. Biol. Chem. 245: 1319-1326. 1970.
Hirota et al., "Isolation of Indolmycin and its Derivatives as Antagonists of L-Tryptophan" Agri. Biol. Chem. 42: 147-151. 1978.
Holmes et al., "Agricultural Use of Burkholderia (Pseudomonas) Cepacia : A Threat to Human Health?", Emerging Infectious Diseases 4: 221-227. 1998.
Hu et al., "Biocidal Activity in Plant Pathogenic Acidovorax, *Burkholderia, Herbaspirillum, Ralstonia, and Xanthomonas*spp" J. Appl. Microbiol. 84: 263-271. 1998.
Huss et al., "Studies on the Spectrophotometric Determination of DNA Hybridization from Renaturation Rates" System. Appl. Microbiol. 4: 184-192. 1983.
Janisiewicz et al., "Biological Control of Blue Mold and Gray Mold on Apple and Pear with Pseudomonas Cepacia" Phytopathology 78: 1697-1700. 1988.
Jansen et al., "Thiangazole: a Novel Inhibitor of HIV-1 from Polyangium Spec" Liebigs Ann. Chem. 4: 357-3359. 1992.
Jeong et al., "Toxoflavin Produced by Burkholderia glumae Causing Rice Grain Rot is Responsible for Inducing Bacterial Wilt in Many Field Crops" Plant Disease 87: 890-895. 2003.
Keum et al., "Effects of Nutrients on Quorum Signals and Secondary Metabolite Productions of *Burkholderia*sp O33," J. Microbiology and Biotechnology 19: 1142-1149. 2009.
Knudsen et al., "Field Persistence and Efficacy of Five Bacterial Preparations for Control of Peanut Leaf Spot" Plant Disease 71: 442-445. 1987.
Koga-Ban et al., "cDNA Sequences of Three Kinds of Beta-Tubulins from Rice" DNA Res. 2: 21-26. 1995.
Koyama et al., "Isolation, Characterization, and Synthesis of Pimprinine, Pimprinethine, and Pimprinaphine, Metabolites of Streptoverticillium Olivoreticuli" Agri. Biol. Chem. 45: 1285-1287. 1981.
Krieg et al., "*Bacillus Thuringiensis* Var. Tenebrionis: Ein Neuer, Gegenuber Larven von Coleopteren Wirksamer Pathotyp" Z. Angew. Entomol. 96: 500-508. 1983.
Kunze et al., "Thiangazole, a New Thiazoline Antibiotic from *Polyangium*sp (Myxobacteria): Production, Antimicrobial Activity and Mechanism of Action" J. Antibiot. 46: 1752-1755. 1993.
Lamichhane et al., "Essential Metabolites of *Mycobacterium Tuberculosis*and their Mimics". mBio 2(1): e00301-10.doi:10.1128/mBio.00301-10. 2011.

(56) References Cited

OTHER PUBLICATIONS

Larossa et al., "The Sulfonylurea Herbicide Sulfometuron Methyl is an Extremely Potent and Selective Inhibitor of Acetolactate Synthase in *Salmonella Typhimurium*", Journal of Biological Chemistry, 259: 8753-8757. 1984.
Lea et al., "The Action of 2-Amino-4-(Methylphosphinyl)-Butanoic Acid (Phosphinothricin) and its 2-Oxo-Derivative on the Metabolism of Cyanobacteria and Higher Plants", Phytochemistry 23: 1-6. 1984.
Lee et al., "Cepacidine A, a Novel Antifungal Antibiotic Produced by Pseudomonas cepacia. 1. Taxonomy, Production, Isolation and Biological Activity", J. Antibiotics 47: 1402-1405. 1994.
Leahy et al., "Comparison of Factors Influencing Trichloroethylene Degradation by Toluene-Oxidizing Bacteria" Appl. Environ. Microbiol. 62: 825-833. 1996.
Lessie et al., "Genomic Complexity and Plasticity of Burkholderia Cepacia" FEMS Microbiol. Lett. 144: 117-128. 1996.
Lindquist et al., "Isolation and Structure Determination of Diazonamides A and B, Unusual Cytotoxic Metabolites from the Marine Ascidian Diazona Chinensis" J. Am. Chem. Soc. 113: 2303-2304. 1991.
Lorch et al., "Basic Methods for Counting Microoganisms in Soil and Water," in *Methods in Applied Soil Microbiology and Biochemistry*. K. Alef and P. Nannipieri. Eds. San Diego, CA, Academic Press: pp. 146-161. 1995.
Lydon et al., "Inhibitors of Glutamine Biosynthesis", in *Plant Amino Acids: Biochemistry and Biotechnology*. B. Singh, Ed. New York, USA, Marcel Decker. 445-464. 1999.
Mahenthiralingam et al., "DNA-Based Diagnostic Approaches for Identification of Burkholderia Cepacia Complex, Burkholderia Vietnamiensis, Burkholderia Multivorans, Burkholderia Stabilis, and Burkholderia Cepacia Genomovars I and III" J. Clin. Microbiol. 38: 3165-3173. 2000.
Mao et al., "Isolation and Characterization of Antifungal Substances from *Burkholderia*sp Culture Broth", Current Microbiology, 53: 358-364. 2006.
Meyers et al., "Xylocandin: A New Complex of Antifungal Peptides. I.Taxonomy, Isolation and Biological Activity", J. Antibiotics, 40: 1515-1519. 1987.
Ming et al., "Metal Binding and Structure-Activity Relationship of the Metalloantibiotic Peptide Bacitracin" J. Inorganic Biochemistry 91: 46-58. 2002.
Moon et al., "Plant Growth Promoting and Fungicidal 4-Quinolinones from Pseudomonas Cepacia", Phytochemistry, 42: 365-368. 1996.
Morita et al., "Biological Activity of Tropolone" Biol. Pharm. Bull. 26: 1487-1490. 2003.
Nagamatsu, "Syntheses, Transformation, and Biological Activities of 7-Azapteridine Antibiotics: Toxoflavin, Fervenulin, Reumycin and their Analogs" Recent Res. Devel. Org. Bioorg. Chem. 4: 97-121. 2001.
Naik, et al., "Pimprinine, an Extracellular Alkaloid Produced by Streptomyces CDRIL-312: Fermentation, Isolation and Pharmacological Activity" J. Biotech. 88: 1-10. 2001.
Nakajima et al., "Hydantocidin: a New Compound with Herbicidal Activity" J. Antibiot. 44: 293-300. 1991.
Nakajima et al., "New Antitumor Substances, FR901463, FR901464 and FR901465. I. Taxonomy, Fermentation, Isolation, Physico-Chemical Properties and Biological Activities" J. Antibiot. 49: 1196-1203. 1996.
Nakajima et al., "New Antitumor Substances, FR901463, FR901464 and FR901465. II. Activities Against Experimental Tumors in Mice and Mechanism of Action" J. Antibiot. 49: 1204-1211. 1996.
N'Diaye et al., "Almazole A and Almazole B, Unusual Marine Alkaloids of an Unidentified Red Seaweed of the Family Delesseriaceae from the Coasts of Senegal" Tet. Lett. 35: 4827-4830. 1994.
Nierman et al., "Structural Flexibility in the Burkholderia Mallei Genome" Proc. Natl. Acad. Sci. USA 101: 14246-14251. 2004.

Okazaki et al., "Rhizobial Strategies to Enhance Symbiotic Interaction: Rhizobitoxine and 1-Aminocyclopropane-1-Carboxylate Deaminase" Microbes Environ. 19: 99-111. 2004.
Parke et al., "Diversity of the Burkholderia Cepacia Complex and Implications for Risk Assessment of Biological Control Strains" Annu. Rev. in Phytopathology 39: 225-258. 2001.
Partida-Martinez et al., "A Gene Cluster Encoding Rhizoxin Biosynthesis in 'Burkholderia Rhizoxina,' the Bacterial Endosymbiont of the Fungus Rhizopus Microsporus", ChemBioChem, 8: 41-45. 2007.
Petit et al. "Isolation of Labradorins 1 and 2 from *Pseudomonas Syringae*pv. corona faciens" J. Nat. Prod. 65: 1793-1797. 2002.
Pitt et al., "Type Characterization and Antibiotic Susceptibility of Burkholderia (*Pseudomonas*) Cepacia Isolates from Patients with Cystic Fibrosis in the United Kingdom and the Republic of Ireland" J. Med. Microbiol. 44: 203-210. 1996.
Ramette et al., "Species Abundance and Diversity of Burkholderia Cepacia Complex in the Environment" Appl. Environ. Microbiol. 71: 1193-1201. 2005.
Reis et al., "*Burkholderia Tropica*sp. nov., a Novel Nitrogen-Fixing, Plant-Associated Bacterium" Int. J. Syst. Evol. Microbiol. 54: 2155-2162. 2004.
Salama et al., "Potency of Spore- γ-Endotoxin Complexes of Bacillus Thuringiensis Against Some Cotton Pests" Z. Angew. Entomol. 91: 388-398. 1981.
Selva et al., "Targeted Screening for Elongation Factor Tu Binding Antibiotics" J. Antibiot. 50: 22-26. 1997.
Selvakumar et al., "Production and Bioassay of Bialaphos Biosynthesized by Streptomyces Hydroscopicus NRRL B-16256," Bioprocess Engineering 20:459-462. 1999.
Shao et al., "Biosynthesis of 2-Hydroxyethyl phosphate, an Unexpected Intermediate Common to Multiple Phosphonate Biosynthetic Pathways," J. Biol. Chem. 283:23161-23168. 2008.
Shoji et al., "Isolation of Cepafungins I, II and III from *Pseudomonas*Species", J. Antibiotics, 43, 783-787. 1990.
Singh et al., "Development of a Simple Assay Protocol for High-Throughput Screening of *Mycobacterium Tuberculosis*Glutamine Synthetase for the Identification of Novel Inhibitors", Journal of Biomolecular Screening, 10(7): 725-729. 2005.
Singh et al., "Development of a Simple High-Throughput Screening Protocol Based on Biosynthetic Activity of *Mycobacterium Tuberculosis*Glutamine Synthetase for the Identification of Novel Inhibitors", J Biomol Screen11: 1035-1042. 2006.
Schweizer, et al., "Mechanisms of antibiotic resistance in Burkholderia pseudomallei : implications for treatment of melioidosis", Future Microbiolo., Dec. 2012, vol. 7. No. 12, pp. 1389-1399.
Stokell, et al., Rapid emergence of a ceftazidime-resistant Burkholderia multivorans strain in a cystic fibrosis patient, J. Cyst. Fibros., Mar. 9, 2013. vol. 12 No. 6, pp. 812-816.
Spilker et al., "PCR-Based Assay for Differentiation of Pseudomonas Aeruginosa from other *Pseudomonas*Species Recovered From Cystic Fibrosis Patients" J. Clin. Microbiol. 42: 2074-2079. 2004.
Stead et al., "Induction of Phenazine Biosynthesis in Cultures of Pseudomonas Aeruginosa by L-N-(3-oxohexanoyl) Homoserine Lactone" FEMS Microbio. Letters 140:15-22. 1996.
Sultan et al., "Novel Oxidized Derivatives of Antifungal Pyrrolnitrin from the Bacterium Burkholderia Cepacia K87," J. Antibiotics 61: 420-425. 2008.
Tachibana et al., "Inhibition of Glutamine Synthetase and Quantitative Changes of Free Amino Acids in Shoots of Bialaphos Treated Japanese Barnyard Millet", J. Pesticide Science, 11:27-31. 1986.
Takahashi et al., "Martefragin A, a Novel Indole Alkaloid Isolated from a Red Alga, Inhibits Lipid Peroxidation" Chem Pharm. Bull. 46: 1527-1529. 1998.
Takita et al., "Chemistry of Bleomycin. XIX Revised Structures of Bleomycin and Phleomycin" J. Antibiot. 31: 801-804. 1978.
Thompson et al., "Spinosad—A Case Study: An Example from a Natural Products Discovery Programme" Pest Management Sci. 56: 696-702. 2000.

(56) References Cited

OTHER PUBLICATIONS

Tran Van et al., "Repeated Beneficial Effects of Rice Inoculation with a Strain of Burkholderia Vietnamiensis on Early and Late Yield Component in Low Fertility Sulphate Acid Soils of Vietnam" Plant and Soil 218: 273-284. 2000.
Tsuruo et al., "Rhizoxin, a Macrocyclic Lactone Antibiotic, as a New Antitumor Agent Against Human and Murine Tumor Cells and their Vincristine-Resistant Sublines" Cancer Res. 46: 381-385. 1986.
Umehara et al., "Studies of New Antiplatelet Agents WS-30581 A and B" J. Antibiot. 37: 1153-1160. 1984.
Ueda et al., "FR901228, a Novel Antitumor Bicyclic Depsipeptide Produced by Chromobacterium violaceum No. 968," J. Antibiotics 47:301-310. 1994.
Vandamme et al. "Polyphasic Taxonomic Study of the Emended Genus *Arcobacter* with *Arcobacter butzleri* comb. nov. and *Arcobacter skirrowii* sp. nov., an Aerotolerant Bacterium Isolated from Veterinary Specimens" Int. J. Syst. Bacteriol. 42: 344-356. 1992.
Vanderwall et al., "A Model of the Structure of HOO-Co Bleomycin Bound to d(CCAGTACTGG): Recognition at the d(GpT)site and Implications for Double-Stranded DNA Cleavage" Chem. Biol. 4: 373-387. 1997.
Vencill et al., "Herbicide Resistance: Toward an Understanding of Resistance Development and the Impact of Herbicide-Resistant Crops", Weed Science. 60: 2-30. 2012.
Vermis et al. "Evaluation of Species-Specific RecA-Based PCR Tests for Genomovar Level Identification Within the Burkholderia Cepacia Complex" J. Med. Microbiol. 51: 937-940. 2002.
Vial et al., "Burkholderia Diversity and Versatility: An Inventory of the Extracellular Products", J. Microbiol. Biotechnol. 17:9. 1407-1429. 2007.
Watanabe et al, "A New Antibiotic SF2583A, 4-Chloro-5-(3'indoly)oxazole, Produced by Streptomyces" Meiji Seika Kenkyu Nenpo 27: 55-62. 1988.
Wayne et al., "Report of the Ad Hoc Committee on Reconciliation of Approaches to Bacterial Systematics" Int. J. Syst. Bacteriology. 37: 463-464. 1987.
Werner et al., "Uptake of Indolmycin in Gram-positive Bacteria." Antimicrob. Agents Chemotherapy 18: 858-862. 1980.
Wilson et al., "Toxicity of Rhizonin A, Isolated from Rhizopus Microsporus, in Laboratory Animals" Food Chem. Toxicol. 22: 275-281. 1984.
Zeck, "A Rating System for Field Evaluation of Root-Knot Nematode Infestations," Pflanzenschutz-Nachrichten Bayer 24,1: 141-144. 1971.
Zhou et al., "Antimicrobial Susceptibility and Synergy Studies of Burkholderia Cepacia Complex Isolated From Patients with Cystic Fibrosis" Antimicrob. Agents and Chemotherapy 51: 1085-1088. 2007.
Extended European Search Report for EP App. No. 11748040.0 dated Jun. 5, 2013.
International Search Report and Written Opinion for Application No. PCT/US2011/026016 dated Jan. 18, 2012.
International Preliminary Report on Patentability for Application No. PCT/US2011/0260126 dated Aug. 28, 2012.
International Search Report and Written Opinion for Application No. PCT/US2012/050807 dated Feb. 26, 2013.
International Search Report and Written Opinion for Application No. PCT/US2014/015799 dated May 27, 2014.
Database EMBL Accession No. AF148554, Jun. 7, 2000.
Database EMBL Accession No. AF265235, Jun. 8, 2001.
Database EMBL Accession No. AB092606, Apr. 2, 2003.
Database EMBL Accession No. AJ420880, Nov. 27, 2001.
Database EMBL Accession No. AF175314, Sep. 5, 2000.
Database EMBL Accession No. AM905038, Nov. 20, 2007.
Database EMBL Accession No. AY740337, Oct. 10, 2004.
Database EMBL Accession No. AB212236, Mar. 28, 2006.
Database EMBL Accession No. AB212227, Mar. 28, 2006.
Database EMBL Accession No. AY741345 Oct. 10, 2004.
Database EMBL Accession No. AB508854, Jul. 2, 2009.
Database EMBL Accession No. AY741351, Oct. 10, 2004.
Database EMBL Accession No. AY741349, Oct. 10, 2004.
Database EMBL Accession No. AY40350, Aug. 31, 2005.
Database EMBL Accession No. AY741334, Oct. 10, 2004.
Database EMBL Accession No. AY741348, Oct. 10, 2004.
Database EMBL Accession No. AY741330, Oct. 10, 2004.
Database EMBL Accession No. AY741340, Oct. 10, 2004.
Database EMBL Accession No. AY741339, Oct. 10, 2004.
Database EMBL Accession No. AM747631, Jun. 27, 2007.
Database EMBL Accession No. AY741359, Oct. 10, 2004.
Database EMBL Accession No. AY741341, Oct. 10, 2004.
Database EMBL Accession No. AY741353, Oct. 10, 2004.
Database EMBL Accession No. AM747632, Jun. 21, 2007.
Database EMBL Accession No. AM747628, Jun. 21, 2007.
Database EMBL Accession No. AY661910, Aug. 3, 2004.
Database EMBL Accession No. FJ932759, Jun. 3, 2009.
Database EMBL Accession No. AM747630, Jun. 21, 2007.
Database EMBL Accession No. EU684748, Jun. 8, 2008.
Database EMBL Accession No. AB021369, Jan. 22, 1999.
Database EMBL Accession No. AY741361, Oct. 10, 2004.
Database EMBL Accession No. AY741335, Oct. 10, 2004.
Database EMBL Accession No. AB211225, Apr. 16, 2005.
Database EMBL Accession No. FJ436055, Dec. 29, 2008.
Database EMBL Accession No. DQ273265, Dec. 7, 2005.
Database EMBL Accession No. GQ359110, Aug. 16, 2009.
Database EMBL Accession No. U96927, Jul. 1, 1998.
Database EMBL Accession No. EU826644, Nov. 3, 2008.
Database EMBL Accession No. E10021, Oct. 8, 1997.
Database EMBL Accession No. AB252073, Aug. 29, 2006.
Database EMBL Accession No. U96928, Jul. 1, 1998.
Database EMBL Accession No. EU305400, Jan. 8, 2008.
Database EMBL Accession No. FJ870663, May 10, 2009.
Database EMBL Accession No. AY662003, Aug. 3, 2004.
Database EMBL Accession No. AJ491304, Jun. 17, 2003.
Database EMBL Accession No. U96937, Jul. 1, 1998.
Database EMBL Accession No. U96929, Jul. 1, 1998.
Database EMBL Accession No. FJ606689, Jan. 20, 2009.
Database EMBL Accession No. AY946011, Mar. 26, 2005.
Database EMBL Accession No. EU214612, Jul. 8, 2008.
Database EMBL Accession No. AY946010, Mar. 26, 2005.

* cited by examiner

USE OF *BURKHOLDERIA* FORMULATIONS, COMPOSITIONS AND COMPOUNDS TO MODULATE CROP YIELD AND/OR CORN ROOTWORM INFESTATION

CROSS REFERENCE TO RELATED APPLICATIONS

This application is a continuation-in-part application of U.S. Ser. No. 14/336,601, filed on Jul. 21, 2014. Ser. No. 14/336,601 is a continuation of Ser. No. 13/843,971, filed on Mar. 15, 2013. Ser. No. 13/843,971 is a continuation-in-part of U.S. Ser. No. 13/034,575 filed on Feb. 24, 2011. Ser. No. 13/034,575 claims the benefit of priority under 37 U.S.C. 119(e) of provisional applications 61/308,287 and 61/406,541, filed on Feb. 25, 2010 and Oct. 25, 2010, respectively. All of the applications are hereby incorporated by reference in their entirety.

TECHNICAL FIELD

Provided is the use of or compositions or formulations comprising *Burkholderia* species, filtrate, supernatant, extract, pesticidally active compound or metabolite derived therefrom as an insecticide, particularly against infestation of *Diabrotica* spp. (Corn Rootworm) and/or as a crop yield enhancer.

BACKGROUND

Commercial crops are often the targets of attack by insects. Insect can have a significant negative effect on crop yield. Chemical insecticides have been effective in eradicating insect infestations; however, there are disadvantages to using chemical insecticides. Chemical insectidal agents are not selective and may exert a negative effect on beneficial insects and other organisms as well as the targeted insect. Chemical insectidal agents may persist in the environment and generally are slow to be metabolized, if at all. They accumulate in the food chain, and particularly in the higher predator species, where they can assert negative effects. Accumulations of chemical insectidal agents also results in the development of resistance to these chemical tools.

The western corn rootworm, *Diabrotica virgifera virgifera* LeConte, is a major pest of corn in the United States. The western corn rootworm overwinters in the egg stage in fields where corn was grown the previous season. The eggs hatch from late May through June. Thereafter, the larvae pass through 3 larval stages, or instars, feeding upon the corn root system. Following completion of larval development, the larvae transform into pupae, which are white and immobile. Adults of western corn rootworms begin to emerge in early July and continue to emerge from the pupae stage into August. Adult beetles feed on the corn foliage and silk. Female beetles lay the vast majority of their eggs in the soil of cornfields during August and early September. Western corn rootworm larvae can survive only on corn and a few other species of Poaceae (Branson and Ortman, J. Econ. Entomol. 60: 201-203 (1967); Branson and Ortman, J. Econ. Entomol. 60: 201-203 (1967)). Larval root feeding decreases plant vigor by reducing the water and nutrients supplied to the developing corn plants. Extensive root damage weakens the root system and makes the plants more susceptible to lodging (plants lean over or elbow), which eventually reduces corn yield and often results in death of the plant. Lodged plants are difficult to harvest resulting in further yield losses. The western corn rootworm adults feed upon corn leaves, which can slow plant growth and, on rare occasions, kill plants of some corn varieties. The western corn rootworm cause economic losses throughout the Midwest and in certain eastern and northeastern states where corn is produced.

Control of corn rootworms has been partially addressed by crop rotation. However, economic demands on the utilization of farmland restrict the use of crop rotation. In addition, the spread of at least one strain of rootworm has been documented in which female oviposition occurs in soybean fields, which further complicates crop rotation strategies. Therefore, chemical insecticides are relied upon most heavily to guarantee the desired level of control. Over $250 million worth of insecticides are applied annually to control corn rootworms alone in the United States. Even with insecticide use, rootworms still can cause over $750 million worth of crop damage each year. The use of chemical insecticides to control corn rootworm has several drawbacks. Continual use of insecticides has allowed resistant insects to evolve. Situations such as extremely high populations of larvae, heavy rains, and improper calibration of insecticide application equipment can result in poor control. Chemical insecticides used for corn rootworm control often raises environmental concerns such as contamination of soil and of both surface and underground water supplies, because many of them are toxic to humans, wildlife and other nontarget species. As a result, much research has been concentrated in the area of biopesticides.

Thus, there is a need for alternative methods for controlling or eradicating insect infestation on or in plants; methods which are selective, environmentally safe, non-persistent, biodegradable, and that fit well into pest resistance management schemes.

Disclosed herein is a non-*Burkholderia cepacia* complex, non-*Burkholderia plantari*, non-*Burkholderia gladioli*, *Burkholderia* sp., in particular, *Burkholderia* A396 sp. nov. *rinojensis* (NRRL Accession No. B-50319, a.k.a., 206) that can decrease *Diabrotica* infestation and/or increase crop yield. It is non-pathogenic to vertebrates, such as birds, mammals and fish, as is described in, for example, U.S. Pub. No. 2011-0207604 and U.S. application Ser. No. 13/843,971. Methods of growing the *Burkholderia* sp. and making a composition of *Burkholderia* sp. and its products (e.g., a whole-cell broth) are also described in U.S. Pub. No. 2011-0207604 and U.S. application Ser. No. 13/843,971.

SUMMARY

Provided herein is a method for increasing yield in *Zea mays* and/or decreasing infestation of corn rootworm larvae in a location where modulation is desired comprising applying an amount of (a) a culture, suspension or whole cell broth comprising a strain of *Burkholderia* sp., or supernatant, filtrate, cell fraction, extract and/or one or more compounds derived from said culture, suspension or whole cell broth and (b) optionally at least one of a carrier, diluent or adjuvant effective to modulate said infestation of corn rootworm larvae at said location. In a particular embodiment, the strain has the identifying characteristics of *Burkholderia* A396 (NRRL Accession No. B-50319).

Infestation of *Diabrotica* (corn rootworm) larvae can be modulated by modulating mortality of corn rootworm larvae, specifically by modulating and particularly increasing or boosting mortality of corn rootworm larvae and/or by decreasing hatching rate of eggs laid and/or decreasing the number of eggs laid in a particular location.

Zea mays yield, measured in Bu/A, can also be modulated by the application of Burkholderia sp. culture.

In one aspect, the present disclosure describes a first embodiment relating to a method for modulating infestation of *Diabrotica* spp. (corn rootworm) in a location where modulation is desired comprising applying an effective amount of (a) a culture, suspension or whole cell broth comprising a strain of *Burkholderia* sp., or supernatant, filtrate, cell fraction, and/or extract derived from said culture, suspension or whole cell broth, and (b) optionally at least one of a carrier, diluent or adjuvant, to modulate said infestation of corn rootworm at said location.

The method according to embodiment 1, wherein the location where modulation is desired is on a plant, plant seed, plant roots, plant part, seedling or substrate for growing said plant.

The method according to embodiment 1, wherein said *Burkholderia* sp. is *Burkholderia* A396 strain.

The method according to embodiment 1, wherein said *Burkholderia* sp. has the identifying characteristics of (NRRL Accession No. B-50319).

The method according to embodiment 1 wherein said *Diabrotica* (corn rootworm) is Western or Northern Corn Rootworm.

The method according to embodiment 1, wherein said *Diabrotica* (corn rootworm) is modulated by modulating the mortality of said corn rootworm.

The method according to embodiment 1, wherein the mortality of *Diabrotica* (corn rootworm) is modulated and wherein there is a mortality of corn rootworm of at least about 50% at said location.

The method according to embodiment 1, wherein the wherein the mortality of corn rootworm is modulated and wherein there is a mortality of *Diabrotica* (corn rootworm) of at least about 50% following application of said culture, suspension or whole cell broth comprising a strain of *Burkholderia* sp., or supernatant, filtrate, cell fraction, extract and/or one or more compounds derived from said culture, suspension or whole cell broth and (b) at least one of a carrier, diluent or adjuvant at said location.

The method according to embodiment 1, which further comprises applying another natural or artificial insecticidal substance.

The method according to embodiment 1, wherein the infestation of *Diabrotica* (corn rootworm) is modulated by modulating the rate of hatching of eggs.

The method according to embodiment 1, wherein said culture, suspension or whole cell broth comprising a strain of *Burkholderia* sp., or supernatant, filtrate, cell fraction, and/or extract derived from said culture, suspension or whole cell broth further comprise at least one of a carrier, diluent or adjuvant is formulated into a composition.

Yet in another aspect, the present disclosure relates to a method for modulating plant yield and *Diabrotica* infestation contemporaneously comprising applying an effective amount of a culture, suspension or whole cell broth comprising a strain of *Burkholderia* sp., or supernatant, filtrate, cell fraction, and/or extract derived from said culture, suspension or whole cell broth to a plant or plant part.

BRIEF DESCRIPTION OF THE FIGURES

FIG. 1 depicts trial two, with increased *Zea mays* yield, with y-axis measured in Bu/A at 15% moisture, by applying *Burkholderia* A396 NRRL Accession No. B-50319 culture (MBI-206) on DKC52-43VT3 corn hybrid. Y-axis is Bu/A. SDTR is seed treatment with Technical grade active ingredients. IF is in-furrow. RW is row feet. Means sharing the same letters are not statistically significant ($P<0.05$).

FIG. 2 depicts trial three, with increased *Zea mays* yield, with y-axis measured in Bu/A at 15% moisture, by applying *Burkholderia* A396 NRRL Accession No. B-50319 culture (MBI-206) on Pioneer 1023AM corn hybrid. Y-axis is Bu/A. SDTR is seed treatment with Technical grade active ingredients. IF is in-furrow. RW is row feet. Means sharing the same letters are not statistically significant ($P<0.1$).

FIG. 3 depicts trial four, with increased *Zea mays* yield, with y-axis measured in Bu/A at 15% moisture, by applying *Burkholderia* A396 NRRL Accession No. B-50319 culture (MBI-206) on DKC Smart Stax corn hybrid. Y-axis is Bu/A. SDTR is seed treatment with Technical grade active ingredients. IF is in-furrow. RW is row feet. Means sharing the same letters are not statistically significant ($P<0.05$).

DETAILED DESCRIPTION OF THE PREFERRED EMBODIMENTS

While the compositions and methods heretofore are susceptible to various modifications and alternative forms, exemplary embodiments will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Where a range of values is provided, it is understood that each intervening value, to the tenth of the unit a value, unless the context clearly dictates otherwise, between the upper and lower limit of that range and any other stated or intervening value in that stated range, is included therein. Smaller ranges are also included. The upper and lower limits of these smaller ranges are also included therein, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms “a,” “and” and “the” include plural references unless the context clearly dictates otherwise.

As defined herein, “derived from” means directly isolated or obtained from a particular source or alternatively having identifying characteristics of a substance or organism isolated or obtained from a particular source. In the event that the “source” is an organism, “derived from” means that it may be isolated or obtained from the organism itself or culture broth, suspension or medium used to culture or grow said organism. A compound “derived from” or “obtainable from” means that a compound may be isolated from or produced by a cell culture, whole cell broth, suspension, filtrate, supernatant, fraction or extract.

As defined herein, “whole broth culture” or “whole cell broth” refers to a liquid culture containing both cells and media. If bacteria are grown on a plate, the cells can be harvested in water or other liquid, whole culture. The terms “whole broth culture” and “whole cell broth” are used interchangeably.

As defined herein, “supernatant” refers to the liquid remaining when cells grown in broth or are harvested in another liquid from an agar plate and are removed by centrifugation, filtration, sedimentation, or other means well known in the art.

As defined herein, "filtrate" refers to liquid from a whole broth culture that has passed through a membrane.

As defined herein, "extract" refers to liquid substance removed from cells by a solvent (water, detergent, buffer, organic solvent) and separated from the cells by centrifugation, filtration or other method.

As defined herein, "metabolite" refers to a compound, substance or byproduct of a fermentation of a microorganism, or supernatant, filtrate, or extract obtained from a microorganism that has pesticidal activity.

As defined herein, an "isolated compound" is essentially free of other compounds or substances, e.g., at least about 20% pure, preferably at least about 40% pure, more preferably about 60% pure, even more preferably about 80% pure, most preferably about 90% pure, and even most preferably about 95% pure, as determined by analytical methods, including but not limited to chromatographic methods, electrophoretic methods. A compound "derived from" a *Burkholderia* sp. species also encompasses a metabolite.

As defined herein, "carrier" is an inert, organic or inorganic material, with which the active ingredient is mixed or formulated to facilitate its application to plant or other object to be treated, or its storage, transport and/or handling.

The term "diluent" is intended to mean an aqueous or non-aqueous solution with the purpose of diluting the active ingredient.

As defined herein, "modulate", is used to mean to alter the amount of a value. For example, decrease in rate of insect infestation or increase in *Zea Mays* yield.

As defined herein, "pest infestation", is the presence of a pest in an amount that causes a harmful effect including an insect such as corn rootworm, a disease or infection in a host population, or emergence of an undesired weed in a growth system.

As defined herein "pesticide", is a substance derived from a biological product or chemical substance that increase mortality or inhibit the growth rate of plant pests and includes but is not limited to nematicides, algaecides, herbicides, insecticides, plant fungicides, plant bactericides, and plant viricides.

The method disclosed herein can comprise or be derived from an organism having the identifying characteristics of a *Burkholderia* species, more particularly, from an organism having the identifying characteristics of a strain of *Burkholderia* A396 (NRRL Accession No. B-50319), or alternatively from any other microorganism. The methods comprise cultivating these organisms and obtaining the compounds and/or compositions by isolating these compounds from the culture of these organisms.

In particular, the organisms are cultivated in nutrient medium using methods known in the art. The organisms can be cultivated by shake flask cultivation, small scale or large scale fermentation (including but not limited to continuous, batch, fed-batch, or solid state fermentations) in laboratory or industrial fermenters performed in suitable medium and under conditions allowing cell growth. The cultivation can take place in suitable nutrient medium comprising carbon and nitrogen sources and inorganic salts, using procedures known in the art. Suitable media are available can be available from commercial sources or prepared according to published compositions.

After cultivation, the compounds, metabolites and/or compositions can be extracted from the culture broth. The extract can be fractionated by chromatography. Compounds used can be metabolites and in a specific embodiment may include but is not limited to compounds set forth in US Patent Application Publication No. US20110207604, US20140073501 and PCT appln. no. PCT/US2014/015799, the contents of all which are published and incorporated herein by reference in their entirety.

The substances set forth above used in the compositions and methods disclosed herein can be formulated in any manner. Non-limiting formulation examples include but are not limited to Emulsifiable concentrates (EC), Wettable powders (WP), soluble liquids (SL), Aerosols, Ultra-low volume concentrate solutions (ULV), Soluble powders (SP), Microencapsulation, Water dispersed Granules, Flowables (FL), Microemulsions (ME), Nano-emulsions (NE), and Seed treatments etc. In any formulation described herein, percent of the active ingredient is within a range of 0.01% to 99.99%.

The compositions can be in the form of a liquid, gel or solid. Liquid compositions comprise pesticidal compounds derived from a *Burkholderia* sp strain, e.g. a strain having the identifying characteristics of *Burkholderia* A396 (NRRL Accession No. B-50319).

A solid composition can be prepared by suspending a solid carrier in a solution of pesticidal compounds and drying the suspension under mild conditions, such as evaporation at room temperature or vacuum evaporation at 65° C. or lower.

A composition can comprise gel-encapsulated compounds derived from the *Burkholderia* strain. Such gel-encapsulated materials can be prepared by mixing a gel-forming agent (e.g., gelatin, cellulose, or lignin) with a culture or suspension of live or inactivated *Burkholderia* sp, or a cell-free filtrate or cell fraction of a *Burkholderia* culture or suspension, or a spray- or freeze-dried culture, cell, or cell fraction or in a solution of pesticidal compounds used in the method of the invention; and inducing gel formation of the agent.

The composition can additionally comprise a surfactant to be used for the purpose of emulsification, dispersion, wetting, spreading, integration, disintegration control, stabilization of active ingredients, and improvement of fluidity or rust inhibition. In a particular embodiment, the surfactant is a non-phytotoxic non-ionic surfactant which preferably belongs to EPA Inerts List 4B. In another particular embodiment, the nonionic surfactant is polyoxyethylene (20) monolaurate. The concentration of surfactants may range between 0.1-35% of the total formulation, preferred range is 5-25%. The choice of dispersing and emulsifying agents, such as non-ionic, anionic, amphoteric and cationic dispersing and emulsifying agents, and the amount employed is determined by the nature of the composition and the ability of the agent to facilitate the dispersion of the compositions of the present invention.

The composition as set forth above also comprises a stabilizing agent, which stabilizes a biological pesticide composition against physical separation and loss of activity due to exposure to sunlight. This stabilizing agent can be a benzoic acid salt or lignin sulfonate salt.

The composition as noted can further comprise an insecticide. The insecticide may include but is not limited to avermectin, Bt, neem oil, spinosads, *Burkholderdia* sp. as set forth in US Patent Appln. Pub. No. 2011-0207604, entomopathogenic fungi such a *Beauveria bassiana* and chemical insecticides including but not limited to organochlorine compounds, organophosphorous compounds, carbamates, pyrethroids, and neonicotinoids.

The composition of the present disclosure contains *Burkholderia* sp. and can be combined with another microorganism and/or pesticide (e.g., nematicide, fungicide, insecticide, herbicide). The microorganism can include, but is not limited to, an agent derived from *Bacillus* sp. (e.g., *B. firmus, B. thuringiensis, B. pumilus, B. licheniformis, B. amyloliquefaciens, B. subtilis*), *Paecilomyces* sp. (*P. lilacinus*), *Pasteuria* sp. (*P. penetrans*), *Pseudomonas* sp., *Brevabacillus* sp., *Lecanicillium* sp., *Ampelomyces* sp., *Pseudozyma* sp., *Streptomyces* sp. (*S. bikiniensis, S. costaricanus, S. avermitilis*), *Trichoderma* sp., *Gliocladium* sp., *avermectin, Myrothecium* sp., *Paecilomyces* spp., *Sphingobacterium* sp., *Arthrobotrys* sp., *Chlorosplrnium* sp, *Neobulgaria* sp, *Daldinia* sp, *Aspergillus* sp, *Chaetomium* sp, *Lysobacter* sp, *Lachnum papyraceum, Verticillium suchlasporium, Arthrobotrys oligospora, Pochonia chlamydosporia* (synonym: *Verticillium chlamydosporium*), *Hirsutella minnesotensis, Hirsutella rhossiliensis, Pleurotus ostreatus, Omphalotus olearius, Lampteromyces japonicas, Brevudimonas* sp., and *Muscodor* sp.

The pesticide can be a natural oil, oil product or chemical pesticide. In particular, the agent can be a natural oil or oil-product having nematicidal, fungicidal and/or insecticidal activity (e.g., paraffinic oil, tea tree oil, lemongrass oil, clove oil, cinnamon oil, citrus oil (including but not limited to bitter orange, orange, lemon) rosemary oil, pyrethrum, allspice, bergamot, blue gum, camomile, citronella, common jasmine, common juniper, common lavender, common myrrh, field mint, freesia, gray santolina, herb hyssop, holy basil, incense tree, jasmine, lavender, marigold, mint, peppermint, pot marigold, spearmint, ylang-ylang tree, and saponins.

The chemical pesticide can be a single site anti-fungal agent which can include but is not limited to benzimidazole, a demethylation inhibitor (DMI) (e.g., imidazole, piperazine, pyrimidine, triazole), morpholine, hydroxypyrimidine, anilinopyrimidine, phosphorothiolate, quinone outside inhibitor, quinoline, dicarboximide, carboximide, phenylamide, anilinopyrimidine, phenylpyrrole, aromatic hydrocarbon, cinnamic acid, hydroxyanilide, antibiotic, polyoxin, acylamine, phthalimide, benzenoid(xylylalanine), a demethylation inhibitor selected from the group consisting of imidazole, piperazine, pyrimidine and triazole (e.g., bitertanol, myclobutanil, penconazole, propiconazole, triadimefon, bromuconazole, cyproconazole, diniconazole, fenbuconazole, hexaconazole, tebuconazole, tetraconazole), myclobutanil, and a quinone outside inhibitor (e.g., strobilurin). The strobilurin can include but is not limited to azoxystrobin, kresoxim-methoyl or trifloxystrobin. In yet another particular embodiment, the anti-fungal agent is a quinone, e.g., quinoxyfen(5,7-dichloro-4-quinolyl 4-fluorophenyl ether). The anti-fungal agent can also be derived from a Reynoutria extract. The chemical pesticide can also be a multi-site non-inorganic, chemical fungicide. For example, the chemical fungicide can be chloronitrile, quinoxaline, sulphamide, phosphonate, phosphite, dithiocarbamate, chloralkythios, phenylpyridin-amine, or cyano-acetamide oxime.

Nematicides can include, but are not limited to, avermectin nematicides (e.g., abamectin); botanical nematicides (e.g., carvacrol); carbamate nematicides (e.g., benomyl carbofuran, carbosulfan, cloethocarb); oxime carbamate nematicides (e.g., alanycarb, aldicarb aldoxycarb, oxamyl tirpate); fumigant nematicides (e.g., carbon disulfide, cyanogen, 1,2-dichloropropane, 1,3-dichloropropene, dithioether, methyl bromide, methyl iodide, sodium tetrathiocarbonate); organophosphorus nematicides, which includes, but are not limited to, organophosphate nematicides (e.g., diamidafos, fenamiphos, fosthietan, phosphamidon); organothiophosphate nematicides (e.g., cadusafos, chlorpyrifos, dichlofenthion dimethoate ethoprophos, fensulfothion, fosthiazate, heterophos, isamidofos, isazofos, phorate, phosphocarb, terbufos, thionazin, triazophos); phosphonothioate nematicides (e.g., imicyafos, mecarphon); and other nematicides (e.g., acetoprole, benclothiaz, chloropicrin, dazomet, DBCP, DCIP, fluensulfone, furfural, metam, methyl isothiocyanate, xylenols, spirotetramat).

The compositions disclosed herein can also be used in combination with other growth promoting agents such as synthetic or organic fertilizers (e.g., di-ammonium phosphate in either granular or liquid form), compost teas, seaweed extracts, plant growth hormones such as IAA (indole acetic acid) used in a rooting hormone treatment for transplants either alone or in combination with plant growth regulators such as IBA (indole butyric acid) and NAA (naphthalene acetic acid), and growth promoting microbes, such as *Bacillus* spp., *Pseudomonads, Rhizobia,* and *Trichoderma* spp.

Furthermore, the compositions can be used in combination with seed-coating agents. Such seed coating agents can include, but are not limited to, ethylene glycol, carboxymethyl cellulose, methyl cellulose, polyethylene glycol, chitosan, carboxymethyl chitosan, peat moss, resins and waxes. The compositions can be applied using methods known in the art. Specifically, these compositions can be applied to and around plants or plant parts. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plants include all parts and organs of plants above and below the ground, such as shoot, leaf, flower and root, examples which may be mentioned being leaves, needles, stalks, stems, flowers, fruit bodies, fruits, seeds, roots, tubers and rhizomes. The plants include, but are not limited to, harvested material, and vegetative and generative propagation material, for example cuttings, tubers, rhizomes, offshoots and seeds.

The compositions, cultures and supernatants and pesticidal compounds set forth above can be used particularly to modulate infestation of corn rootworm larvae on a plant, plant seed, plant part, plant roots. seedling or substrate (e.g., soil, sand, loam, clay) for growing said plant, particularly a corn plant, cucurbits (e.g., cucumbers, melons, pumpkins, squash, gourds, etc.), wheat, barley, oats, rye, sorghum, beans and legumes, peas, potato, sweet potato, soy, oilseed rape, tomato, aubergine, lettuce, pepper, sunflower, and ornamental plants such as chrysanthemum as well as other plants such as red root pigweed (*Amaranthus retroflexus*), goosegrass (*Eleusine indica*) weeping lovegrass (*Eragrostis curvula*), sand lovegrass (*Eragrostis trichodes*), rhodes grass (*Chloris gayana*), shattercane (*Sorghum drummondii*), johnsongrass (*Sorghum halepense*), maize (*Zea mays*), sandbur (*Cenchrus tribuloides*), large crabgrass (*Digitaria sanquinalis*), barnyard grass, (*Echinochloa crus-galli*), woolly cupgrass (*Eriochloa villosa*), witchgrass (*Panicum capillare*), foxtail millet (*P. italicum*), Prosso millet (*P. miliaceum*), switchgrass (*P. virgatum*), giant foxtail (*Setaria faberi*), yellow foxtail (*S. pumila*), bristly foxtail (*S. vericillatta*), Green foxtail (*S. viridis*), texas panicum (*Urochloa texana*), Redtop (*Agrostis gigantean*), oat (*Avena sativa*), reed canarygrass (*Phalaris arundinacea*), downy brome (*Bromus tectorum*), Orchardgrass (*Dactylis glomerate*), western wheatgrass (*Pascopyrum smithii*), spring wheat "Russ" (*Triticum aestivum*)

The present disclosure also relates to the use of *Burkholderia* sp. to modulate members go the genus *Diabrotica* (rootworm) including *Diabrotica balteata* (banded cucumber beetle), *Diabrotica barberi* (northern corn rootworm), *Diabrotica beniensis, Diabrotica cristata, Diabrotica curvipustulata, Diabrotica dissimilis, Diabrotica elegantula, Diabrotica emorsitans, Diabrotica graminea, Diabrotica hispanolae, Diabrotica lemniscata, Diabrotica linsleyi, Diabrotica longicornis, Diabrotica milleri, Diabrotica nummularis, Diabrotica occlusa, Diabrotica porracea, Diabrotica scutellata, Diabrotica speciosa* (cucurbit beetle or chrysanthemum beetle), *Diabrotica tibialis, Diabrotica trifasciata, Diabrotica undecimpunctatahowardi* (southern corn rootworm, a.k.a spotted cucumber bettle), *Diabrotica undecimpunctata tenella* (western cucumber beetle), *Diabrotica undecimpunctata undecimpunctata* (western spotted cucumber beetle), *Diabrotica virgifera virgifera* (western corn rootworm), *Diabrotica virgifera zea* (Mexican corn rootworm), *Diabrotica viridula, Diabrotica significata* (three-spotted cucumber beetle)

In a particular embodiment, infestation of corn rootworm larvae is modulated by modulating mean mortality of said larvae at a particular location, particularly at least about 10%, 20%, 30%, 40%, 50%, 60%, 70%, 80% and more particularly at least about 90% within at least following application of said compositions, cultures and supernatants and pesticidal compounds set forth above.

Application of an effective controlling amount of *Burkholderia* sp. for *Diabrotica* spp. is also provided herein. A substantially pure culture, whole cell broth, supernatant, filtrate, extract or compound of the bacterial strain can be applied, alone or in combination with another substance, in an effective pest control or pesticidal amount. An "effective amount" is defined as the quantity of microorganism cells, supernatant, whole cell broth, filtrate, cell fraction or extract, metabolite and/or compound alone or in combination with another pesticidal substance that is sufficient to modulate plant corn rootworm infestation. The amount that will be within an effective range can be determined by laboratory or field tests by those skilled in the art. In an embodiment of the invention, when the composition is applied directly to the seed, the effective amount is a concentration of about 0.01%-30% of the active ingredient *Burkholderia* sp. per 100 g of seed. In another embodiment, the effective amount is a concentration of about 0.05%-25%, or about 0.1%-20%, or about 0.5%-15%, or about 1%-10%, or about 2%-5% of the active ingredient per 100 g of seed. In yet another embodiment, the effective amount is a concentration of about 0.5% to 1% of the active ingredient per 100 g of seed. In another embodiment of the invention, when the composition is applied to the soil by, for example, in furrow, the effective amount is about 0.1-50 oz. of the active ingredient per 1000 ft row. In other embodiments, the effective amount for soil application is about 1-25 oz. of the active ingredient per 1000 ft row. In yet another embodiment, the effective amount is about 2-20 oz, or about 3-15 oz, or about 4-10 oz, or about 5-8 oz, of the active ingredient per 1000 ft row. Yet in another embodiment, the effective amount is about 14 or 28 oz./1000 ft row.

The compositions, substantially pure culture, whole cell broth, supernatant, filtrate extract or compounds set forth above can modulate corn root worm infestation by a number of mechanisms. These include but are not limited to exterminating the plant parasitic at various stages of the life cycle (eggs, larvae or adult), affecting the motility of the plant parasitic, and/or reducing the number and/or viability of eggs that are laid by the parasitic.

The said formulated product can be used alone or sequentially with one or more other components as set forth above, such as growth promoting agents in a tank mix or in a program (sequential application called rotation) with predetermined order and application interval during the growing season.

Contact of the plants with the compositions set forth above can be carried out directly or by allowing the compositions to act on their surroundings, habitat or storage space by, for example, immersion, spraying, evaporation, fogging, scattering, painting on, injecting or soil amendment. In the case that the composition is applied to a seed, the composition can be applied to the seed as one or more coats prior to planting the seed using one or more coats using methods known in the art.

The compositions comprising *Burkholderia* sp. can be applied by root dip at transplanting, specifically by treating a fruit or vegetable with the composition by dipping roots of the fruit or vegetable in a suspension of said composition (about 0.25 to about 1.5% and more particularly about 0.5% to about 1.0% volume by volume) prior to transplanting the fruit or vegetable into the soil.

Alternatively, the composition can be applied by drip or other irrigation system. Specifically, the composition comprising *Burkholderia* sp. can be injected into a drip irrigation system. In a particular embodiment, the composition may be applied at a rate of about 11 to about 4 quarts per acre.

In yet another embodiment, the composition can be added as an in-furrow application. Specifically, the composition can be added as an in-furrow spray at planting using nozzles calibrated to deliver a total output of 2-6 gallons/acre, or at outputs of up to 20 gallons per acre. Nozzles are placed in the furrow opener on the planter so that the pesticide application and seed drop into the furrow are simultaneous. The mixtures set forth above and, where appropriate, a solid or liquid adjuvants are prepared in known manner. For example, the mixtures can be prepared by homogeneously mixing and/or grinding the active ingredients with extenders such as solvents, solid carriers and, where appropriate, surface-active compounds (surfactants). The compositions can also contain further ingredients such as stabilizers, viscosity regulators, binders, adjuvants as well as fertilizers or other active ingredients in order to obtain special effects.

Yet in another embodiment, the compositions from *Burkholderia* sp. can increase plant yield, such as measured in bu/A at 15% moisture for *Zea mays*, while providing CRW infestation modulation.

In one embodiment, the present microbial components can be formulated as dusts or powders, water dispersible formulations, emulsions, solutions, baits and fumigants or aerosols. In addition to the active ingredient, these formulations include carriers, solvents, emulsifiers, wetting agents, dispersing agents, stickers, UV screens, and other inert ingredient to maintain stability and shelf-life of the active ingredient. These additional ingredient preferably are selected from those listed in EPA Inert List 4a (www.epa-.gov/opprd001/inerts/inerts_list4Acas.pdf) for conventional formulations and 4b (www.epa.gov/opprd001/inerts/inerts_list4Bname.pdf) for organic formulations.

EXAMPLES

The composition and methods set forth above will be further illustrated in the following, non-limiting Examples.

The examples are illustrative of various embodiments only and do not limit the claimed invention regarding the materials, conditions, weight ratios, process parameters and the like recited herein.

Example 1

Four field trials were established in the Midwestern United States to test the efficacy of several insecticide treatments in protecting corn roots from damage by corn rootworm larvae. Experimental trial design in each case was a randomized complete block with 6 replications per treatment. Individual plots were 5-10' wide×25-30' in length. Corn hybrids were selected for the trials and could be either conventional (non-GMO traited) hybrids or GMO-traited hybrids containing, at a minimum, one or more corn rootworm control traits (Table 1). The between row spacing in each case was 30" thus individual plots were made up of either 2 or 4 rows per trial. Planting depth was 1-2" and planting population per acre was between 28,700 and 34,000 seeds per acre. Normal agronomic practices regarding tillage, fertility, non-target pest control and crop production were followed in each trial.

TABLE 1

| Ref. # | Corn Hybrid | Corn Traits in Seed | Seed Trt. in Bag |
|---|---|---|---|
| Trial 1 | Blue River 56M30 | None | None |
| Trial 2 | DKC52-43VT3 | AGP (2), CRW (1), RR | Comprehensive |
| Trial 3 | Pioneer 1023AM | AGP (2), RR, LL | Comprehensive |
| Trial 4 | DKC Smart Stax | AGP (3), CRW (2), RR, LL | Comprehensive |

AGP = traits for above-ground pests like European Corn Borer, Corn earworm, etc. Number in parentheses indicates number of traits.
CRW = Corn Rootworm
RR = Roundup Ready (glyphosate) herbicide tolerant
LL = Liberty Link (gluphosinate) herbicide tolerance 'Comprehensive' seed treatment generally includes one or more fungicides, insecticides and possibly even nematicide components to protect seed from feeding from diseases and below-ground pests like wireworm, seed corn maggot, etc Treatments included: an untreated check; MBI-206 (also known as *Burkholderia* A396); MBI-206BM3SE1(a.k.a *Burkholderia* A396 or Venerate® XC, also see FIGS. 1-3) applied at 14 or 28 ounces of formulated product per 1000 row ft. in-furrow; and an in-furrow competitive (commercial) standard (Capture LFR @ 0.4-0.49 oz/1000 row feet or Lorsban 4E @ 8 oz/1000 row feet). A subsample of the selected hybrid seed were sent to Marrone Bio Innovations in Davis, Calif. for seed coating in the laboratory. These treated seed were then returned for planting.

Root feeding damage by corn rootworm larvae was assessed by digging root systems 53-86 days after planting, washing them, and measuring them using the Iowa State University 0-3 Corn Rootworm Damage scale where 0, 1, 2 & 3 equate to the number of root nodes completely chewed off by corn rootworm larvae; i.e. the greater the number the more intense the feeding damage. Yield measurements (bushels/acre at 15% moisture) where taken occurred at harvest.

Results

In ¾ studies there was heavy CRW pressure and feeding damage. In 1 of those locations seed was planted having CRW traits and still sustained heavy CRW damage. This indicates resistance to the CRW traits in this hybrid. Overall the product treatments performed better than the UTC (un-treated control). There did not appear to be a consistent rate effect for the ones applied in-furrow. Table 2 summarized the results, where SDTR=seed treatment. Trial 2 has light CRW (corn Rootworm) infestation. The Table indicates *Burkholderia* A396's activity against CRW, especially under heavy CRW pressure.

TABLE 2

| Treatment/Rate | Type | Trial 1 | Trial 2 | Trial 3 | Trial 4 | Avg. All | Avg. 3 trials with Heavy CRW |
|---|---|---|---|---|---|---|---|
| Untreated Check | — | 2.24 | 0.32 | 2.25 | 2.12 | 1.73 | 2.20 |
| MBI-206 BM3SE1 @ 14 oz/1000 row ft. | In-Furrow | 0.81 | 0.27 | 0.56 | 0.72 | 0.59 | 0.70 |
| MBI-206 BM3SE1 @ 28 oz/1000 row ft. | In-Furrow | 1.15 | 0.21 | 1.05 | 0.67 | 0.77 | 0.96 |
| MBI-206 Low Rate | SDTR | 1.06 | 0.22 | 0.82 | 0.72 | 0.71 | 0.87 |
| MBI-206 High Rate | SDTR | 1.18 | 0.25 | 0.69 | 0.56 | 0.67 | 0.81 |
| Commercial Standard | In-Furrow | 0.19 | 0.23 | 0.88 | 0.44 | 0.44 | 0.50 |

FIGS. 1-3 (trials 2-4) demonstrates that while *Burkholderia* A396 (206) modulates CRW infestation, it can also increase overall *Zea mays* yield in Bu/A. Almost all of the IF applications of *Burkholderia* A396 presents statistically the same, or statistically more, than the chemical or untreated control.

Example 2

Formulation and Application of Pesticidal Toxins (206) as Powders and Dusts

These are simple formulations that usually contain 0.1-25% of the active ingredient *Burkholderia* A396 (206). However, more active ingredient can be used depending on the potency and particular application. The pesticide toxin is mixed with a solid carrier, which can be of small particle size. Solid carriers can include: silicate clays (e.g., attapulgite, bentonites, volcanic ash, montmorillionite, kaolin, talc, diatomites, etc.), carbonates (e.g., calcite, dolomite, etc), synthetics (precipitated silica, fumed silica, etc.), ground botanicals (e.g., corn cob grits, rice hulls, coconut shells, etc.), organic flour (e.g., Walnut shell flour, wood bark, etc.) or pulverized mineral (e.g., Sulphur, diatomite, tripolite, lime, gypsum talc, pyrophyllite, etc.). The inert ingredients used in dust formulations can also come from those listed in EPA Inert List 4a (www.epa.gov/opprd001/inerts/inerts_list4Acas.pdf) for conventional formulations and 4b (www.epa.gov/opprd001/inerts/inerts_list4Bname.pdf) for organic formulations. Small particle size can be achieved by mixing the active with the carrier and pulverizing in a mill.

Dusts are defined as having a particle size less than 100 microns and with increase in particle size the toxicity of the formulation decreases. In the selection of a dust formulation its compatibility, fineness, bulk density, flow ability, abrasiveness, absorbability, specific gravity and cost should be taken into consideration.

| Formulation components | Formulation A | Formulation B | Formulation C | Formulation D |
|---|---|---|---|---|
| Active ingredient | 0.65 | 5 | 10 | 25 |
| Talc | | | 90 | |
| Kaolin or other clay | | 95 | | |

A dust formulation can also be prepared from a dust concentrate (e.g., 40% active ingredient, 5% stabilizer, 20% silica, 35% magnesium carbonate) added at 1-10% to a 1:1 organic filler/talc combination. The dust formulation is used as a contact powder (CP) or tracking powder (TP) against crawling insects. A dust formulation with high flowability can be applied by pneumatic equipment in greenhouses.

Example 3

Formulation of Pesticidal Toxins as Granules or Pellets

The present microbial component (206, a.k.a. Burkholderia A396) is applied in liquid form to coarse particles of porous material (e.g., clay, walnut shells, vermiculite, diatomaceous earth, corn cobs, attapulgite, montmorillioinite, kaolin, talc, diatomites, calcite, dolomite, silicas, rice hulls, coconut shells, etc.). The granules or pellets can be water dispersible, and can be formed by extrusion (for pesticidal actives with low water solubility), agglomeration or spray drying. Granule can also be coated or impregnated with a solvent based solution of the pesticidal toxin. The carrier particles can be selected from those listed in EPA Inert List 4a (www.epa.gov/opprd001/inerts/inerts_list4Acas.pdf) for conventional formulations and 4b (www.epa.gov/opprd001/inerts/inerts_list4Bname.pdf) for organic formulations. The active can be absorbed by the carrier material or coat the surface of the granule. Particle size can vary from 250 to 1250 microns (0.25 mm to 2.38 mm) in diameter. The formulations usually contain 2 to 10 percent concentration of the toxicant. The granules are applied in water or whorls of plant or to soil at the rate of 10 kg/ha. Granular formulations of systemic insecticides are used for the control of sucking and soil pest by application to soil. Whorl application is done for the control of borer pests of crops such as sorghum, maize and sugarcane, etc. These types of formulations reduce drift and allow for slower release of the pesticide active.

Granular pesticides are most often used to apply chemicals to the soil to control weeds, fire ants, nematodes, and insects living in the soil or for absorption into plants through the roots Granular formulations are sometimes applied by airplane or helicopter to minimize drift or to penetrate dense vegetation. Once applied, granules release the active ingredient slowly. Some granules require soil moisture to release the active ingredient. Granular formulations also are used to control larval mosquitoes and other aquatic pests. Granules are used in agricultural, structural, ornamental, turf, aquatic, right-of-way, and public health (biting insect) pest control operations.

Application of granular formulations is common in pre-emergence herbicides or as soil insecticides for direct application and incorporation into soil or other solid substrates where plants grow. Granules or pellets can also be applied in-furrow. Granules are commonly used for application top water, such as in flooded rice paddies.

A typical granule formulation includes (% w/w) 1-40% active ingredient, 1-2% stabilizer, 0-10% resin or polymer, 0-5% surfactant, 0-5% binder and is made up to 100% with the carrier material.

Example 4

Formulation of Pesticidal Toxins as Wettable Powders

Wettable powder is a powdered formulation which yields a rather stable suspension when diluted with water. It is formulated by blending the toxicant with diluents such as attapulgite, a surface active agent and an auxiliary material such as sodium salts of sulfo acids. Sometimes stickers are added to improve retention on plants and other surfaces. Wettable powders can be prepared by mixing the pesticidal toxin (10-95%) with a solid carrier, plus 1-2% of a surface-active agent to improve suspensibility. The overall composition of the formulation will include the active ingredient in solid form (5.0-75%), an anionic dispersant and an anionic/nonionic wetting agent.

A typical example of wettable powder formulation will include 10-80% active ingredient, 1-2% wetting agents (e.g., benzene sulphonates, naphthalene sulphonates, aliphatic suplhosuccinates, aliphatic alcohol etoxylates, etc.), 2-5% dispersing agent (e.g., lignosulphonates, naphthalene sulphonate-formaldehyde condensates, etc.), 0.1-1% antifoaming agent, made up to 100% with an inert filler or carrier (e.g., diatomaceous earth, silica, etc.).

Example 5

Formulation of Pesticidal Toxins as Emulsifiable Concentrates

It is a concentrated pesticide formulation containing organic solvent and a surfa-active agent to facilitate emulsification with water. When EC formulations are sprayed on the plant parts, the solvent evaporates quickly leaving a deposit of toxicant from which water also evaporates. Some of the emulsifying agents in insecticide formulations are alkaline soaps, organic amines, sulfates of long chain alcohols and materials such as alginates, carbohydrates, gums, lipids and proteins. Emulsifying agents can be selected from those listed in EPA Inert List 4a (www.epa.gov/opprd001/inerts/inerts_list4Acas.pdf) for conventional formulations and 4b (www.epa.gov/opprd001/inerts/inerts_list4Bname.pdf) for organic formulations.

Example 6

Formulation of Pesticidal Toxins as Solutions

It is a concentrated liquid pesticide formulation (206) that can be used directly or require diluting (soluble concentrates). Soluble concentrates and solutions are water or solvent based mixture with complete miscibility in water.

A typical example of a solution concentrate formulation include 20-70% active ingredient, 5-15% wetting agent, 5-10% antifreeze, and is made up to 100% with water or a water miscible solvent.

Depending on the nature and stability of the pesticidal toxin, a solution formulation might also include thickeners, preservatives, antifoam, pH buffers, UV screens, etc.

Example 7

Formulation of Pesticidal Toxins in Fertilizers Mixtures

The mixture generally constitutes addition of a granular insecticide to chemical fertilizer or spreading of insecticide directly on to the fertilizer. They are applied at the regular fertilizing time and provide both plant nutrients and control of soil insects. Urea 2% solution is mixed with compatible insecticidal emulsions and sprayed for supply of nitrogen to the plant and for realizing effective pest control. Many pesticides are rapidly broken down when mixed with fertilizers.

Example 8

Formulation of Pesticidal Toxins as Poison Baits

The poison baits consist of a base or carrier material attractive to the pest species and a chemical toxicant in relatively small quantities. The poison baits are used for the control of fruit flies, chewing insects, wireworms, white grubs in the soil, household pests rats in the field and slugs. This method is ideal under conditions where spray application is rather difficult. For successful poison baiting the attractiveness, palatability, toxicity, stability and physical condition of the baits, as also the time, place and method of exposure must be considered. The common base used in dry baits is wheat bran moistened with water and molasses an attractant and a toxicant. For the control of fruit sucking moths fermenting sugar solution or molasses with a toxicant is used.

Example 9

Formulation of Pesticidal Toxins into Seed Treatments

Seed treatments include the application of the pesticidal toxins, or other bioactive, antagonistic or symbiotic agents to the surface of the see prior to sowing. The pesticidal toxins, proteins, compound of the invention can be applied to seeds as dry powders, slurried powders or sprayed on the seed before planting.

The pesticidal toxins can be formulated for seed treatments in any of the following modes: dry powder, water slurriable powder, liquid solution, flowable concentrate or emulsion, emulsion, microcapsules, gel, water dispersible granules.

In the case of a dry powder, the active ingredient in formulated similarly to a wettable powder, but with the addition of a sticking agent, such as mineral oil, instead of a wetting agent. For example: One Kg of purified talc powder (sterilized for 12 h), 15 g calcium carbonate, and 10 g carboxy methyl cellulose were mixed under aseptic conditions following the method described by Nandakumar et al (2001). Protein, nucleic acid suspensions or organisms expressing these were mixed in a 1:2.5 ratio (suspension to dry mix) and the product was shade dried to reduce moisture content to 20-35%.

There are several ways in which seed can be treated with the formulations:

Priming: seeds are soaked in double the volume of sterile distilled water containing bacterial/protein/nucleic acid suspensions or talc formulation (dry formulation) (4-10 g kg-1 of seed, depending on seed size) and incubated at $25\pm2°$ C. for 12-24 h. The suspension is drained off and the seeds are dried under shade for 30 min and used for sowing.

Coating: for seed coating different stickers are used, within them, methyl cellulose, alginate, carrageenan and polyvinyl alcohol. These are mixed at percentages between 1-10% as water based solutions and stored at room temperature before application to the seeds. Seeds are soaked in sticker solution (3 ml/100 seeds) for 15 min, scooped out and mixed with organic matter (1.5 g/100 seeds) in plastic bags and shaken vigorously. This process can be automated using a seed coating machine.

What is claimed is:

1. A method for modulating infestation of *Diabrotica* (corn rootworm) in a location where modulation is desired comprising
    applying an effective amount of
    (a) a whole cell broth collected from fermentation of *Burkholderia* A396 NRRL Accession No. B-50319, and
    (b) at least one of a carrier, diluent or adjuvant, to modulate said infestation of corn rootworm at said location.

2. The method according to claim 1, wherein the location where modulation is desired is on a plant, plant seed, plant roots, plant part, seedling or substrate for growing said plant.

3. The method according to claim 1 wherein said *Diabrotica* (corn rootworm) is Western or Northern Corn Rootworm.

4. The method according to claim 1, wherein said *Diabrotica* (corn rootworm) is modulated by modulating the mortality of said corn rootworm.

5. The method according to claim 1, wherein the mortality of *Diabrotica* (corn rootworm) is modulated and wherein there is a mortality of corn rootworm of at least about 50% at said location.

6. The method according to claim 1, wherein the mortality of corn rootworm is modulated and wherein there is a mortality of *Diabrotica* (corn rootworm) of at least about 50% following application of said whole cell broth.

7. The method according to claim 1, which further comprises applying another natural or artificial insecticidal substance.

8. The method according to claim 1, wherein said whole cell broth is formulated into a composition.

9. A method for modulating plant yield and *Diabrotica* infestation comprising
    applying an effective amount of a whole cell broth collected from fermentation of *Burkholderia* A396 NRRL Accession No. B-50319 to a plant or plant part.

* * * * *